US012630323B2

(12) United States Patent
Lindblad et al.

(10) Patent No.: US 12,630,323 B2
(45) Date of Patent: May 19, 2026

(54) PACKAGING MACHINE COMPRISING A DISINFECTION/STERILIZATION STATION, DISINFECTION/STERILIZATION STATION AND METHOD FOR DISINFECTION/STERILIZING IN A PACKAGING MACHINE

(71) Applicant: Tetra Laval Holdings & Finance S.A., Pully (CH)

(72) Inventors: Ulf Lindblad, Bjärred (SE); Mårten Regner, Lund (SE); Jenny Lindblad, Bjärred (SE); Bo Runnberg, Smedstorp (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 362 days.

(21) Appl. No.: 17/915,272

(22) PCT Filed: Mar. 23, 2021

(86) PCT No.: PCT/EP2021/057437
§ 371 (c)(1),
(2) Date: Sep. 28, 2022

(87) PCT Pub. No.: WO2021/197928
PCT Pub. Date: Oct. 7, 2021

(65) Prior Publication Data
US 2023/0136844 A1 May 4, 2023

(30) Foreign Application Priority Data
Apr. 3, 2020 (EP) ..................................... 20167928

(51) Int. Cl.
*B65B 55/10* (2006.01)
*A61L 2/208* (2026.01)
(Continued)

(52) U.S. Cl.
CPC .............. *B65B 55/10* (2013.01); *A61L 2/208* (2013.01); *A61L 2/26* (2013.01); *B65B 43/14* (2013.01);
(Continued)

(58) Field of Classification Search
CPC ..... B65B 55/10; B65B 55/025; B65B 59/003; B65B 59/04; B65B 43/14; A61L 2/26;
(Continued)

(56) References Cited

U.S. PATENT DOCUMENTS 4,512,951 A * 4/1985 Koubek .................... A61L 2/06
422/33
4,631,173 A * 12/1986 Muller .................... B65B 55/10
422/28
(Continued)

FOREIGN PATENT DOCUMENTS

JP 2003525643 A 9/2003
WO 2009/011635 A1 1/2009

OTHER PUBLICATIONS

International Search Report for corresponding Application No. PCT/EP2021/057437, mailed Oct. 6, 2021.

*Primary Examiner* — Anna K Kinsaul
(74) *Attorney, Agent, or Firm* — Renner, Otto, Boisselle & Sklar, LLP

(57) ABSTRACT

A packaging machine configured to form, fill, and seal individual packages is provided. The packaging machine includes a disinfection/sterilization station configured to treat ready-to-fill packaging containers passing through said disinfection station. The disinfection/sterilization station includes a supply section configured to provide gaseous sterilizing agent into open ends of the ready-to-fill packaging containers passing the supply section, and a holding section arranged downstream the supply section. The packaging machine is configured to keep the ready-to-fill pack-
(Continued)

aging containers at the supply section such that the sterilizing agent will condense on areas of the ready-to-fill packaging container having a temperature below the dew point of the sterilizing agent, and the packaging machine is configured to keep the ready-to-fill packaging containers at the holding section such that the gaseous sterilizing agent will treat areas of the ready-to-fill packaging container having a temperature above the dew point of the sterilizing agent.

18 Claims, 4 Drawing Sheets

(51) Int. Cl.

| | |
|---|---|
| *A61L 2/26* | (2006.01) |
| *A61L 101/02* | (2006.01) |
| *A61L 103/00* | (2026.01) |
| *B65B 43/14* | (2006.01) |
| *B65B 51/14* | (2006.01) |
| *B65B 55/02* | (2006.01) |
| *B65B 59/00* | (2006.01) |
| *B65B 59/04* | (2006.01) |

(52) U.S. Cl.
CPC .......... *B65B 51/144* (2013.01); *B65B 55/025* (2013.01); *B65B 59/003* (2019.05); *B65B 59/04* (2013.01); *A61L 2101/02* (2020.08); *A61L 2103/23* (2026.01)

(58) Field of Classification Search
CPC ... A61L 2/208; A61L 2101/02; A61L 2202/23
See application file for complete search history.

(56) References Cited

U.S. PATENT DOCUMENTS

| | | | | |
|---|---|---|---|---|
| 4,742,667 | A | 5/1988 | Mueller | |
| 4,797,255 | A * | 1/1989 | Hatanaka | B65B 55/103 |
| | | | | 422/292 |
| 4,992,247 | A * | 2/1991 | Foti | B65B 55/10 |
| | | | | 53/425 |
| 5,152,968 | A | 10/1992 | Foti | |
| 5,173,259 | A * | 12/1992 | Bordini | A61L 2/20 |
| | | | | 53/167 |
| 5,178,841 | A * | 1/1993 | Vokins | B65B 55/10 |
| | | | | 53/425 |
| 5,488,811 | A * | 2/1996 | Wang | G01N 15/082 |
| | | | | 53/425 |
| 6,039,922 | A * | 3/2000 | Swank | B65B 61/186 |
| | | | | 53/425 |
| 6,056,918 | A * | 5/2000 | Palaniappan | B65B 61/186 |
| | | | | 53/565 |
| 6,094,887 | A * | 8/2000 | Swank | B65B 55/04 |
| | | | | 53/167 |
| 6,120,730 | A * | 9/2000 | Palaniappan | B65B 55/10 |
| | | | | 53/167 |
| 6,183,691 | B1 * | 2/2001 | Swank | B65B 55/10 |
| | | | | 422/298 |
| 6,682,696 | B1 | 1/2004 | Bjerborn | |
| 10,858,133 | B2 * | 12/2020 | Weiler | B67C 7/0073 |
| 11,324,845 | B1 * | 5/2022 | Ricciardi | A61L 2/06 |
| 2004/0081579 | A1 * | 4/2004 | Bjerborn | B65B 55/103 |
| | | | | 264/340 |
| 2006/0008383 | A1 * | 1/2006 | Moller | B65B 55/025 |
| | | | | 422/62 |
| 2006/0067856 | A1 * | 3/2006 | Martensson | B65B 31/025 |
| | | | | 422/295 |
| 2009/0071104 | A1 * | 3/2009 | Fischer | A61L 2/22 |
| | | | | 53/426 |
| 2010/0021359 | A1 * | 1/2010 | Auer | B65B 55/025 |
| | | | | 422/291 |
| 2012/0087829 | A1 * | 4/2012 | Lindblad | B65B 31/041 |
| | | | | 422/302 |
| 2017/0341791 | A1 * | 11/2017 | Weiler | B65B 55/027 |

* cited by examiner

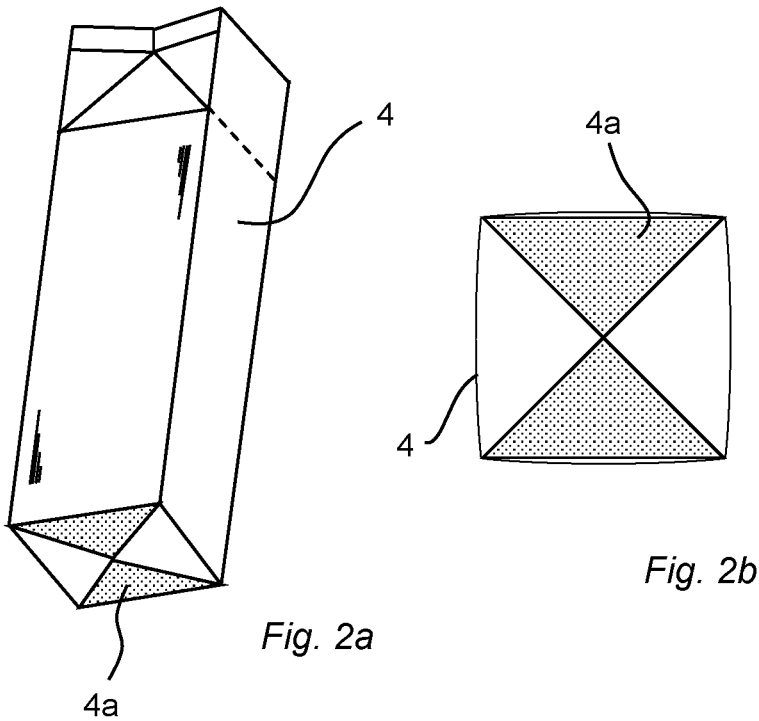
4
4a
4
4a
*Fig. 2a*
*Fig. 2b*
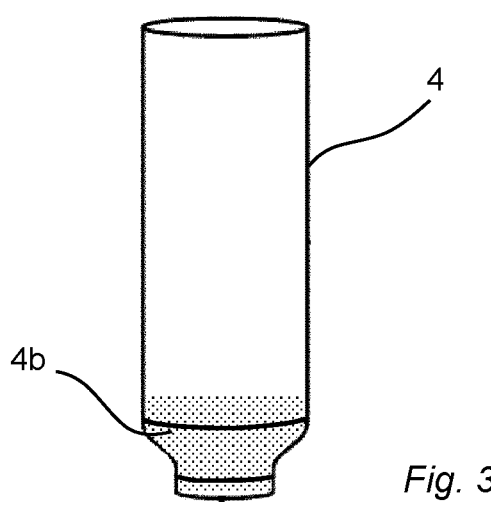
4
4b
*Fig. 3*

PACKAGING MACHINE COMPRISING A DISINFECTION/STERILIZATION STATION, DISINFECTION/STERILIZATION STATION AND METHOD FOR DISINFECTION/STERILIZING IN A PACKAGING MACHINE

TECHNICAL FIELD

The invention relates to a packaging machine, in particular to a packaging machine being configured to form, fill, and seal individual packages. The present invention also relates to a method for such packaging machine.

BACKGROUND ART

Within the food industry, beverages and other products are often packed in paper or paperboard based packages. Packages intended for liquid food are often produced from a packaging laminate comprising a core layer of paper or paperboard and an outer, liquid-tight layer of thermoplastic material on at least that side of the core layer which will form the inside of the packages.

One kind of frequently occurring packages are produced from so-called ready-to-fill packages. Such a ready-to-fill package is produced from a sleeve of packaging laminate like the one described above, being sealed at its bottom end prior to filling. Another type of ready-to-fill package is produced by from an open-ended sleeve of a packaging laminate, and arranging, e.g. by injection molding, a plastic top at the upper end of the sleeve thereby leaving the bottom end open for filling.

The upper end of the ready-to-fill package may consequently be formed by sealing and forming the upper end of the sleeve after filling, or by adding an upper part in the form of e.g. a plastic top prior to filling; the upper end/part may be provided with an opening/closing means, such as a screw cap.

For the ready-to-fill package type described above having the closed bottom end, the open-ended packaging material sleeve is received at an infeed station of the packaging machine, whereafter the bottom end is sealed; the semi-finished package has at this point a shape being ready to fill, however further processes are required to provide a hygienic packaging.

The same applies for the plastic top type of package described above. The open-ended packaging material sleeve is received at an infeed station of the packaging machine, whereafter the upper end is sealed by arranging the plastic top onto the packaging material sleeve; the semi-finished package has at this point a shape being ready to fill, however further processes are required to provide a hygienic packaging.

At a downstream station, the ready-to-fill packages are sterilized or disinfected at least on the inside in order to extend the shelf-life of the product to be stored in the packages. Depending on the desired length of shelf-life, and depending on whether the packages are to be distributed and stored in a refrigerated environment or at room temperature, different levels of sterilization/disinfection are required. Sterilization/disinfection is performed using a gaseous sterilization agent, such as $H_2O_2$.

After sterilization/disinfection of the packages, they are further transported to a filling zone for product filling, a sealing zone for sealing of the open end, and typically also to a final forming zone for final forming of the package.

During disinfection/sterilization, the dew point of the $H_2O_2$ gas needs to be high in order to secure condensation of the $H_2O_2$ on the entire inside surface of the ready-to-fill package. Such disinfection/sterilization technique of condensation is highly efficient, but requires a generally low and uniform temperature of the target to be treated in order to accurately control the disinfection/sterilization process.

As explained above, before filling of the ready-to-fill package closing the end of the packaging laminate sleeve is performed by processes requiring heating. For packages having the bottom end sealed the sealing process is performed by folding the bottom end area of the sleeve to the desired flat bottom shape, and applying heat to melt at least a part of the thermoplastic material of the packaging laminate such that the bottom end is sealed.

For packages having the upper end closed, the process is typically performed by arranging the upper edge of the packaging laminate sleeve in a mold, and injecting melted polymer to form an injection molded plastic top at the upper end of the packaging laminate sleeve.

Hence, immediately after closing one end of the packaging laminate sleeve, which corresponds to the moment when the ready-to-fill package enters disinfection/sterilization, the temperature of the ready-to-fill package will not be uniform. Instead, the areas around the recently closed end of the ready-to-fill package will have an elevated temperature compared to the remaining parts of the ready-to-fill package.

There is a risk that the elevated temperature of the closed end, and the areas of the ready-to-fill package in close vicinity to the closed end, is higher than the dew point of the sterilizing agent, i.e. the $H_2O_2$ gas. In such case the desired level of disinfection/sterilization cannot be guaranteed for the elevated temperature areas of the ready-to-fill package.

In view of the great advantages of disinfection/sterilization utilizing condensation of a gaseous sterilizing agent like $H_2O_2$, there is a need for a solution eliminating the risk of non-sufficient disinfection/sterilization for ready-to-fill packages, especially when the ready-to-fill packages have a non-uniform temperature when entering the disinfection/sterilization station of the packaging machine.

SUMMARY

It is an object of the invention to at least partly overcome one or more of the above-identified limitations of the prior art. In particular, it is an object provide a packaging machine being capable of ensuring a required disinfection/sterilization of ready-to-fill packages even when there is a risk that parts of the ready-to-fill package has a temperature being above the dew point of the sterilizing agent.

To solve these objects a packaging machine is provided. The packaging machine is configured to form, fill, and seal individual packages whereby the packaging machine comprises a disinfection/sterilization station configured to provide a flow of gaseous sterilizing agent towards open ends of ready-to-fill packaging containers passing through said disinfection station. The packaging machine further comprises a supply section configured to provide gaseous sterilizing agent into open ends of the ready-to-fill packaging containers passing the supply section, and a gas holding section arranged downstream the supply section. The packaging machine is configured to keep the ready-to-fill packaging containers at the supply section such that the sterilizing agent will condense on areas of the ready-to-fill packaging container having a temperature below the dew point of the sterilizing agent, and the packaging machine is further configured to keep the ready-to-fill packaging containers at the holding section such that the gaseous steriliz-ing agent will treat areas of the ready-to-fill packaging container having a temperature above the dew point of the sterilizing agent.

The supply section may be configured to supply an amount of gaseous sterilizing agent being sufficient to allow continued condensation on areas of the ready-to-fill pack-aging container having a temperature below the dew point of the sterilizing agent, when the ready-to-fill packaging con-tainers are at the holding section.

The disinfection/sterilization station may further com-prise a first venting section downstream the holding section.

The packaging machine may be configured to keep the ready-to-fill packaging containers at the first venting section such that the gaseous sterilizing agent inside the ready-to-fill packaging container is removed.

The packaging machine may be configured to keep the ready-to-fill packaging containers at the first venting section such that at least a part of the water content of the condensed sterilizing agent is evaporated and removed from the ready-to-fill packaging container.

The disinfection/sterilization station may further com-prise a film holding section downstream the first venting section.

The packaging machine may be configured to keep the ready-to-fill packaging containers at the film holding section such that the condensed film of sterilizing agent, having an increased concentration of sterilizing agent due to the opera-tion of the first venting station, is allowed to treat the inside of the ready-to-fill packaging container.

The disinfection/sterilization station may further com-prise a drying section downstream the film holding section.

The packaging machine may be configured to keep the ready-to-fill packaging containers at the drying section such that the condensed film of sterilizing agent is evaporated completely from the inside of the ready-to-fill packaging container.

According to a second aspect, a disinfection/sterilizing station is provided for use in a packaging machine. The disinfection/sterilizing station comprises a supply section configured to provide gaseous sterilizing agent into open ends of ready-to-fill packaging containers passing the supply section, and a gas holding section arranged downstream the supply section. The ready-to-fill packaging containers are controlled to be kept at the supply section such that the sterilizing agent will condense on areas of the ready-to-fill packaging container having a temperature below the dew point of the sterilizing agent, and the ready-to-fill packaging containers are controlled to be kept at the holding section such that the gaseous sterilizing agent will treat areas of the ready-to-fill packaging container having a temperature above the dew point of the sterilizing agent.

According to a third aspect, a method for disinfection/sterilization in a packaging machine configured to form, fill, and seal individual packages is provided. The method com-prises supplying a gaseous sterilizing agent to the area to be disinfected/sterilized, allowing the gaseous sterilizing agent to at least to some extent condensate at a first sub-area having a temperature below the dew point of the gaseous sterilizing agent, and immediately after condensation, keep-ing a second sub-area, having a temperature above the dew point of the gaseous sterilizing agent, exposed to the remain-ing gaseous sterilizing agent.

The method may further comprise moving the area to be disinfected/sterilized from a supply section, supplying the gaseous sterilizing agent, to a holding section, at which the second sub-area is exposed to the remaining gaseous ster-ilizing agent.

The sterilizing agent may be hydrogen peroxide.

The area to be disinfected/sterilized may be a ready-to-fill packaging container being formed, filled, and sealed by the packaging machine.

The method may further comprise venting the area to be disinfected/sterilized after keeping the second sub-area exposed to the remaining gaseous sterilizing agent such that at least a part of the water content of the condensed sterilizing agent is evaporated and removed from the area, and optionally keeping the area to be disinfected/sterilized in a controlled atmosphere such that the condensed film of sterilizing agent, having an increased concentration of ster-ilizing agent due to the previous venting, is allowed to treat the area.

Still other objectives, features, aspects and advantages of the invention will appear from the following detailed description as well as from the drawings.

BRIEF DESCRIPTION OF THE DRAWINGS

Embodiments of the invention will now be described, by way of example, with reference to the accompanying sche-matic drawings, in which

FIG. 2a is an isometric view of a ready-to-fill package to be treated by a packaging machine according to an embodi-ment;

FIG. 2b is a top view of the ready-to-fill package shown in FIG. 2a;

FIG. 3 is an isometric view of a ready-to-fill package to be treated by a packaging machine according to an embodi-ment;

DETAILED DESCRIPTION

Figure 1:
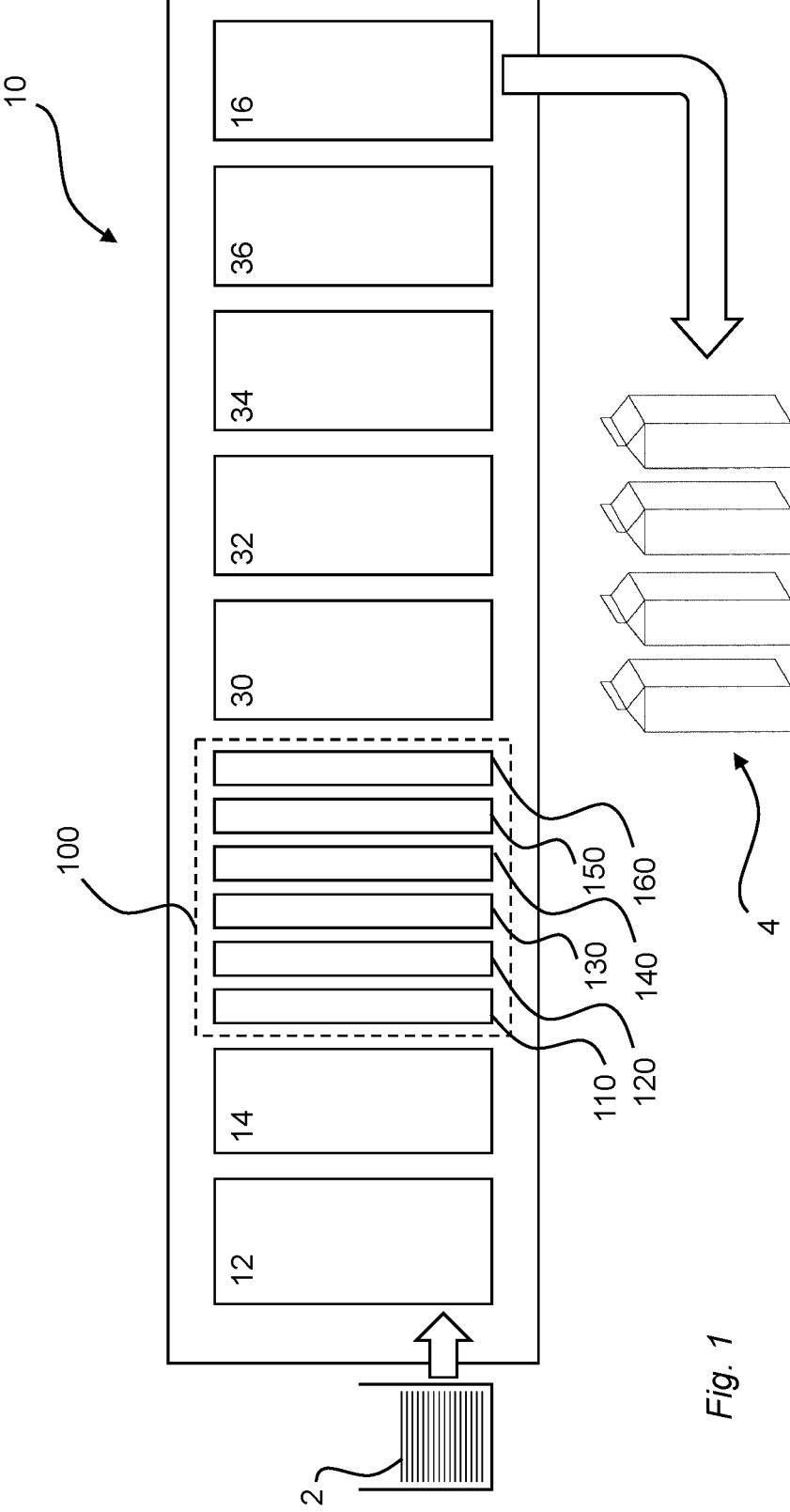
FIG. 1 is a schematic view of a packaging machine according to an embodiment.

With reference to FIG. 1 a packaging machine 10 is shown schematically. The packaging machine 10, being configured to form, fill, and seal packages 4, has an infeed station 12 in which blanks 2 of packaging material, prefer-ably a packaging laminate, are received. The blanks 2 are typically produced as sleeves of a carton-based packaging material, as is well known in the art and already described briefly in the background section. The infeed station 12 is arranged upstream an end sealing station 14, in which the blanks 2 are erected to a sleeve-shape, and in which station one end of each blank is sealed to form a semi-finished package having one end being closed, while the opposite end is still open. As described in the background section, the sealing station 14 may in one embodiment be configured to form a flat bottom end of the packaging material, and heat seal the packaging material to form the closed bottom end. Optionally, in one embodiment the sealing station 14 is configured to insert the upper end of the sleeve in a mold, and provide a plastic top to the sleeve by injection molding directly onto the packaging material. In both examples mentioned, the result will be a semi-finished packaging container having one end closed, and one end still open for later filling.

The semi-finished packages are transported to a disinfection/sterilization station 100, in which the amount of living micro-organisms is reduced. As explained in the background section, the level of disinfection/sterilization may vary depending on user objectives. Disinfection/sterilization of the packaging material is accomplished by means of treatment with a sterilizing agent, such as H2O2 (hydrogen peroxide).

As will be explained in the following, in particular with reference to FIGS. 4 and 5, the disinfection/sterilization station comprises at least an upstream supply section 110, providing a flow of gaseous sterilizing agent, and a holding section 120 arranged downstream the supply station 110. Also, the disinfection/sterilization station 100 comprises a section 130 for condensate film enriching and gas venting, a condensate film holding section 140, a drying section 150, and a venting section 160.

A hygienic chamber may be provided downstream the disinfection station 100. The hygienic chamber comprises further stations of the packaging machine; immediately downstream the disinfection/sterilization station 100 a filling station 30 is arranged. Here, the ready-to-fill packages are filled with their desired content. After filling, the packages may be transported to a pre-folding station 32 in which the upper part of the open-ended package is formed to a desired shape. After pre-forming the packages are transported to a heating station 34 in which heat-sealable material of the packaging material is heated to an elevated temperature. The elevated temperature of the upper end of the packages facilitates sealing of the upper end when the packages enter the sealing station 36 arranged immediately after the heating station 34.

Optionally, pre-folding station 32 and heating station 34 may be configured to form and seal the bottom end of the packaging container 4 in case the upper end has been provided with a plastic top, as explained earlier.

Once sealed, the packages 4 no longer require hygienic conditions whereby they exit the hygienic chamber. At the end of the packaging machine 10, an outfeed station 16 is arranged which is configured to discharge the finished packages 4 from the packaging machine 10 to downstream equipment, storage, and/or transport.

Now turning to FIGS. 2a-b a ready-to-fill packaging container 4 is shown. The packaging container 4 is suitable for being disinfected/sterilized by the disinfection/sterilizing station 100 according to embodiments of the present invention. The ready-to-fill packaging container 4 is shown in a state immediately before entering the disinfection/sterilization station 100, i.e. just after heat sealing of the bottom end 4a. Due to the exposure to heat during the heat sealing, the bottom end 4a will have certain areas elevated temperature, as indicated by the patterned areas in FIGS. 2a-b. It should be noted that in FIG. 2b, the inside of the packaging container 4 is shown thus indicating the elevated temperature on the inside surface of the packaging container 4 to be disinfected/sterilized.

In FIG. 3 another example of a ready-to-fill packaging container 4 is shown, also being suitable for disinfection/sterilization by the disinfection/sterilizing station 100 according to embodiments of the present invention. The ready-to-fill packaging container 4 is shown in a state immediately before entering the disinfection/sterilization station 100, i.e. just after the upper end 4b is provided as a plastic top. Due to the exposure to heat during the heat sealing, the upper end 4b will have certain areas of elevated temperature, as indicated by the patterned area in FIG. 3.

Figure 4:
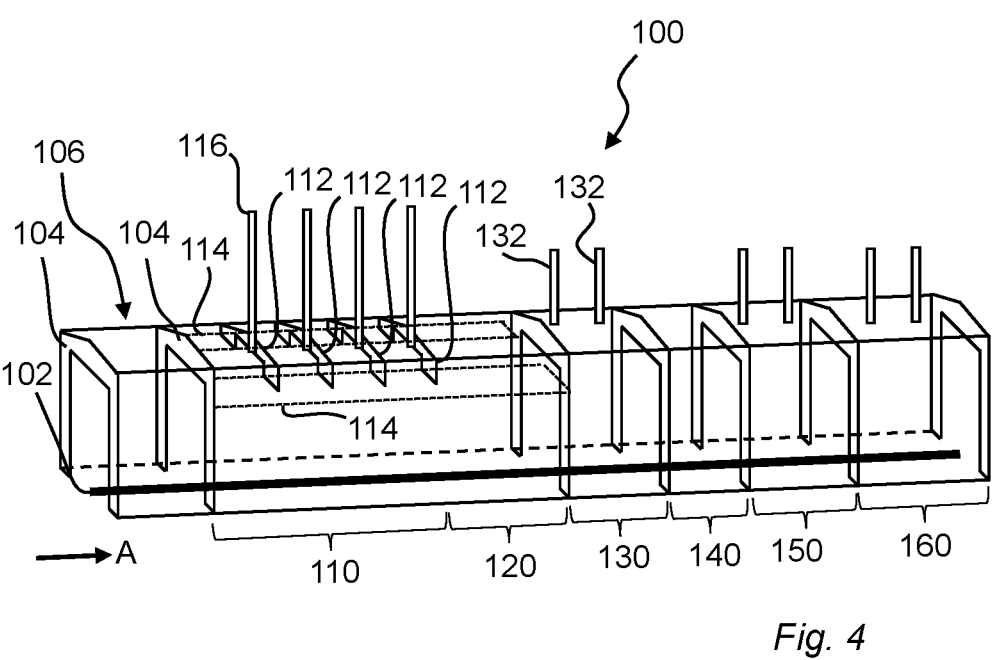
FIG. 4 is a schematic isometric view of a disinfection/sterilization station forming part of a packaging machine according to an embodiment.

Now turning to FIG. 4 an embodiment of a disinfection/sterilization station 100 is shown. As can be seen, the disinfection station 100 has the shape of a tunnel. Ready-to-fill packages (not shown) are fed into the disinfection station 100 from the left side of the drawing. The ready-to-fill packages are transported by a conveyor 102 in the direction of the arrow A, and the conveyor 102 is provided with a series of consecutive cassettes; each cassette is carrying a ready-to-fill package. For illustrative purpose the conveyor 102 is shown only schematically, while the cassettes and the carried packaging containers are not shown. Conveyors of this type, including the cassettes, are well known in the art and will not be described further herein.

As can be seen in FIG. 4, the disinfection/sterilization station 100 is provided with a number of baffles plates. Two vertical baffle plates 104 are provided at the inlet side of the disinfection/sterilization station 100, extending from the bottom portion of the tunnel to the upper portion of the tunnel. The baffle plates 104 are separated in the machine direction, and the space formed between those two baffle plates 104 acts as an entry section 106 of the disinfection/sterilization station 100.

Downstream the entry section 106, the supply section 110 is arranged. The purpose of the supply section 110 is to provide a flow of gaseous sterilizing agent, preferably H2O2 at a concentration of 5000-25000 ppm, such that the interior, as well as the exterior, of the ready-to-fill packages 4 entering the disinfection/sterilization station 100 is treated.

The disinfection/sterilization station 100, and in particular the supply section 110, is preferably provided as a continuous tunnel where an atmosphere of high and relatively uniform concentration of gaseous sterilizing agent is created in the vertically upper gassing portion in order to establish a controlled and even gas distribution into the packages to obtain the required disinfection effect.

Vertical baffle plates 112 are provided at the upper portion of the supply section 110. The baffle plates 112 of the supply section 110 extend upwards from horizontally arranged baffle plates 114. The horizontal baffle plates 114 are spaced apart such that cassettes and ready-to-fill packaging containers can pass between the horizontal baffle plates 114.

The vertical baffle plates 112 of the supply section 110 divide the space inside the tunnel in four distinct index positions. Each index position is associated with a gas supply tube 116 (only one being indicated by reference numeral), preferably arranged at the longitudinal position of the vertical baffle plates 112. Hence, four ready-to-fill packaging containers can be positioned at the index positions at the same time, whereby the gas supply tubes 116 are activated to supply the gaseous sterilizing agent towards the interior of the ready-to-fill packaging containers. However, four distinct positions for the supply section 110 is not required, but in one embodiment the two downstream supply tubes 116 are deactivated such that these two downstream index positions are instead included in the following gas holding section 120, optionally still having the vertical baffle plates 112 in place. It is thus possible to provide the disinfection/sterilization station 100 in a modular setup, such that the exact configuration of the different sections 110-160 can be adjusted and varied within the geometries of the disinfection/sterilization station 100.

As sterilizing agent enters the ready-to-fill packaging container at the supply section 110, the sterilizing agent will condense on areas of the ready-to-fill packaging container having a temperature below the dew point of the sterilizing agent. As explained earlier, these low-temperature areas are the majority of the inside surface of the ready-to-fill packaging container, except the certain parts (i.e. the bottom end just recently being closed by heat sealing or the upper end being provided with an injection molded plastic top) having an elevated temperature, that is, having a temperature above the dew point of the sterilizing agent.

In more detail, the supply section 110 is configured to supply an amount of gaseous sterilizing agent being sufficient to allow continued condensation on the areas of the ready-to-fill packaging container having a temperature below the dew point of the sterilizing agent. At the same time the amount of gaseous sterilizing agent is sufficient to build up the required gas concentration inside the packaging container to also treat the areas having a temperature being higher than the dew point of the gaseous sterilizing agent, which disinfection/sterilization then is performed by gas phase disinfection.

Still referring to FIG. 4, immediately downstream the index positions of the supply section 110 there is a gas holding section 120; the function of the gas holding section 120 being obtaining the desired disinfection/sterilization of the ready-to-fill packages. In particular, when the ready-to-fill packaging containers are arranged at the gas holding section 120, the gaseous sterilizing agent will treat the areas of the ready-to-fill packaging container having a temperature above the dew point of the sterilizing agent.

There is thus a double action disinfection process; low temperature areas will be treated by a condensed film of sterilizing agent while higher temperature areas will be treated by gas phase sterilizing agent.

A first venting section 130 is arranged downstream the holding section 120. The first venting section 130 comprises ventilation means 132 for increasing the concentration of the sterilizing agent in the condensed film. The time during which the ready-to-fill packages are stationary at the venting section 130 is set so that the gaseous sterilizing agent inside the ready-to-fill packaging container 4 is removed. At the same time, at least a part of the water content of the condensed sterilizing agent on the areas of low temperature areas is evaporated and removed from the ready-to-fill packaging container.

Downstream the first venting section 130 a film holding section 140 is provided, for keeping the condensed film of sterilizing agent for a certain amount of time. At the film holding section 140, the condensed film of sterilizing agent, having an increased concentration of sterilizing agent due to the operation of the first venting station 130, is allowed to treat the inside of the ready-to-fill packaging container. The increased disinfection efficiency is thereby obtained by securing sufficient exposure time of the concentrated condense film on these surfaces of the ready-to-fill packaging container.

A drying section 150 is arranged downstream the film holding section 140, which purpose is to allow the condensed film of sterilizing agent to evaporate completely from the inside of the ready-to-fill packaging container.

A final/second venting section 160 is arranged downstream the drying section 150, to remove all gas from the ready-to-fill packaging containers before they exit the disinfection/sterilization station 100.

Figure 5:
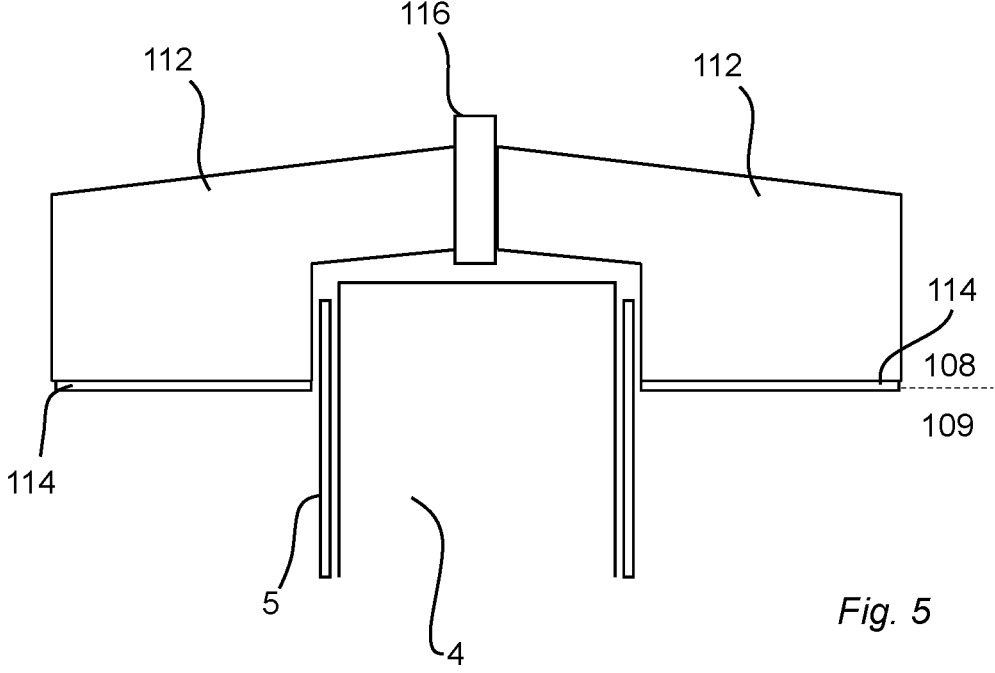
FIG. 5 is a cross-sectional view of parts of the disinfec-tion/sterilization station shown in FIG. 4.

Now turning to FIG. 5, a cross-section of the supply section 110 is shown. The ready-to-fill package 4 is carried by the cassette 5, which extends almost along the entire vertical extension of the ready-to-fill package 4. The cassette

5 is in turn driven by the conveyor (see FIG. 4), which is connected to the bottom portion of the cassette 5.

The gas supply tube 116 is directed downwards, thereby allowing gaseous sterilizing agent to enter the ready-to-fill package 4 such that the interior will be disinfected/sterilized. The horizontal baffle plates 114 assist in delimiting an upper disinfection chamber 108 from a lower chamber 109. As the jet of gaseous sterilizing agent, being discharged from the supply tube 116, will draw surrounding gas/air into the packaging container 4, the horizontal baffle plates 114 will prevent air from below the baffle plates 114 to be drawn into the packaging container, which otherwise would dilute the supplied sterilizing agent.

The vertical baffle plates 112 have a corresponding functionality, as they prevent air/gas from outside the baffle plates to be drawn into the packaging container. Also the sidewalls of the packaging containers 4 assist in forming this boundary between the upper disinfection chamber from the lower chamber. While the concentration of sterilizing agent can be relatively constant in the upper disinfection chamber 108, the concentration in the lower chamber 109 is close to zero.

Figures 6, 7:
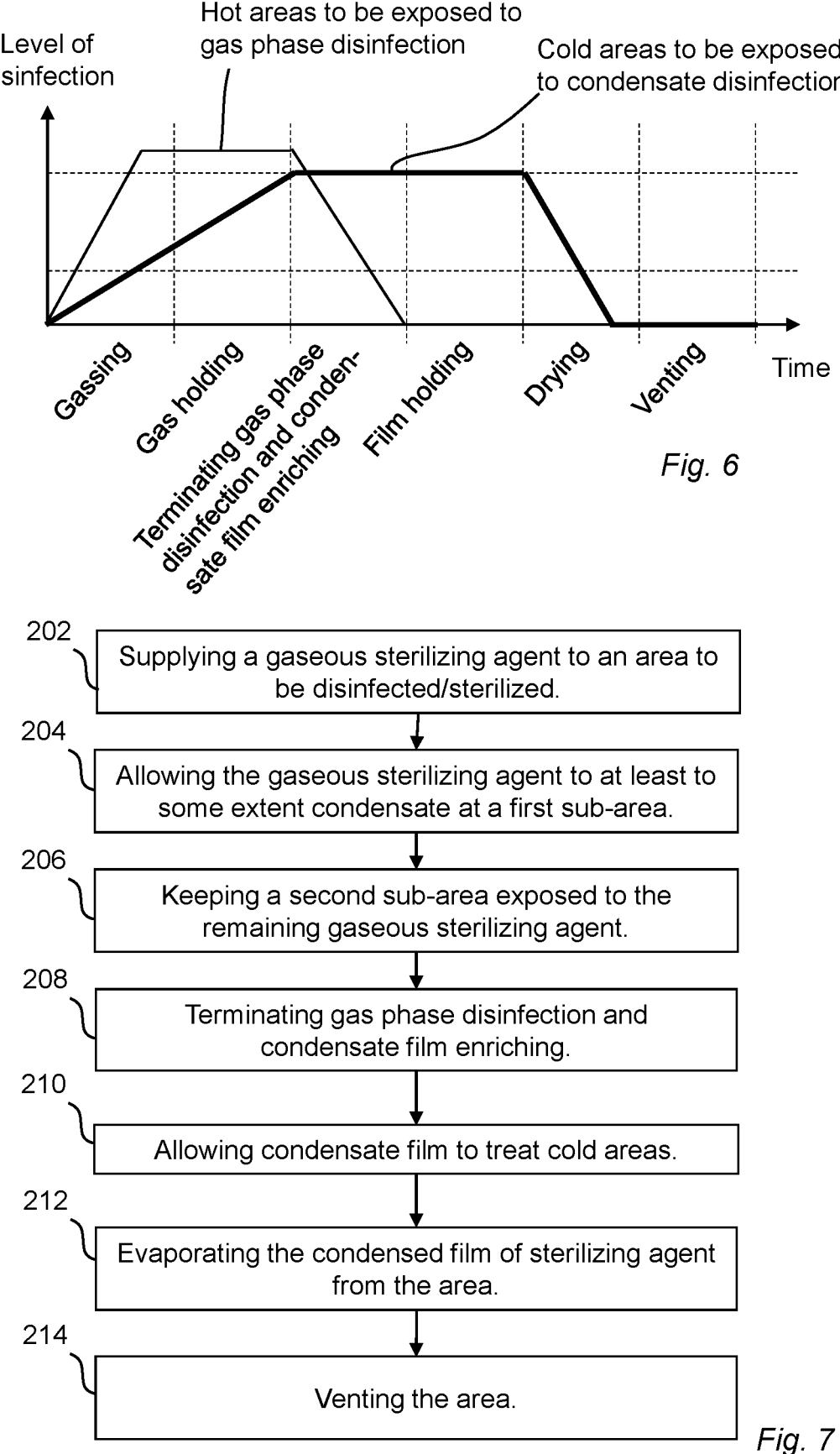
FIG. 6 is a diagram showing disinfection/sterilization as a function of time.
FIG. 7 is a schematic view of a method according to an embodiment.

Now turning to FIG. 6 a diagram is shown, illustrating the disinfection/sterilization process for the different areas of the inside of the packaging container. The diagram shows the process over time.

Two lines are plotted. The thicker line represents the disinfection process for the areas of the inside surface of the ready-to-fill packaging container having a temperature below the dew point of the injected gaseous sterilizing agent, while the thinner line represents the disinfection process for the areas of the inside surface of the ready-to-fill packaging container having a temperature above the dew point of the injected gaseous sterilizing agent.

Starting to the left in the diagram, the first thing to happen is that the ready-to-fill packaging container is moved to an index position of the supply section 110 which injects the gaseous sterilizing agent into the cavity formed by the ready-to-fill packaging container. At the low temperature areas, i.e. the majority of the inside of the packaging container, the sterilizing agent will condense to a film. At the high temperature areas there will be no condensing, but these areas will instead be subject to the gas phase sterilizing agent.

Disinfection/sterilization will continue during the gas holding phase, during which the conditions inside the packaging container remain relatively constant. This means that during this phase, condensed film of sterilizing agent will continue to build on the low temperature areas while at the same time the required gas exposure time is provided for the areas to be exposed to gas phase disinfection/sterilization.

In the subsequent venting phase the gaseous content is removed from the inside of the packaging container which means that disinfection/sterilization of the high temperature areas, having no condensed film, will be finished. For the low temperature areas the venting phase will increase the concentration of the sterilizing agent in the film to some extent.

The next phase, film holding, allows the condensed film to further treat the low temperature areas to be disinfected/sterilized before the next drying phase. Here, the condensed film of sterilizing agent is evaporated, and any remaining sterilizing agent is removed in the final venting phase.

As is clear from FIG. 6 the process of disinfecting/sterilizing the interior of the ready-to-fill packages is very different for different sub-areas; of the entire inside surface area, one sub-area of low temperature (below the dew point of the gaseous sterilizing agent) and one sub-area of high temperature (above the dew point of the gaseous sterilizing agent). Instead of applying a single disinfection/sterilization process, the station 100 is designed so that these different sub-areas can be treated appropriately using a combination of condensed film and gas phase disinfection, occurring simultaneously.

Now, with reference to FIG. 7, a method 200 for disinfecting/sterilizing will be described. The method 200 is preferably performed in a packaging machine being configured to form, fill, and seal individual packaging containers for liquid food. The method 200 is used to disinfect/sterilize (depending on desired shelf life of the final product to be enclosed by the packaging container) the inside surface of ready-to-fill packaging containers before they are filled, and the method 200 is based on the combination of condensing and gas phase disinfection/sterilization in order to overcome difficulties due to the temperature variations of the object to be disinfected/sterilized.

In a first step 202 a gaseous sterilizing agent is supplied to the area to be disinfected/sterilized, i.e. to the interior of a ready-to-fill packaging container. During a following step 204, which is performed immediately once the gaseous sterilizing agent is supplied, the gaseous sterilizing agent is allowed to at least some extent condensate at a first sub-area having a temperature below the dew point of the gaseous sterilizing agent. This sub-area normally represents the majority of the inside surface of the packaging container.

Immediately after condensation, a step 206 is performed of keeping a second sub-area, having a temperature above the dew point of the gaseous sterilizing agent, exposed to the remaining gaseous sterilizing agent. This second sub-area normally corresponds to specific areas being exposed to elevated temperature (such as during a heat sealing process or injection molding process) prior to the start of the method 200.

After step 206 a step 208 of venting the area to be disinfected/sterilized is performed, such that at least a part of the water content of the condensed sterilizing agent is evaporated and removed from the area. Importantly, during this step 208 gas phase disinfection is terminated while the condensate film on the low temperature areas is enriched.

A step 210 is then performed of keeping the area to be disinfected/sterilized in a controlled atmosphere such that the condensed film of sterilizing agent, having an increased concentration of sterilizing agent due to the previous venting, is allowed to treat the area.

In step 212 a drying process is performed, causing evaporation of the condensed film of sterilizing agent from the area. Step 212 is preferably followed by a final venting step 214, in which all remaining sterilizing agent is removed.

For the described method 200, all steps are preferably including a movement of the ready-to-fill packaging container such that it travels through dedicated sections of a disinfection/sterilizing station 100, as described above.

From the description above follows that, although various embodiments of the invention have been described and shown, the invention is not restricted thereto, but may also be embodied in other ways within the scope of the subject-matter defined in the following claims.

The invention claimed is:

1. A packaging machine configured to form, fill, and seal individual packages, comprising a disinfection/sterilization station configured to treat ready-to-fill packaging containers passing through said disinfection/sterilization station, wherein the disinfection/sterilization station comprises a supply section configured to provide gaseous sterilizing agent into open ends of the ready-to-fill packaging containers passing the supply section, and a holding section arranged downstream the supply section, whereby the packaging machine is configured to keep the ready-to-fill packaging containers at the supply section such that the gaseous sterilizing agent will condense on areas of the ready-to-fill packaging container having a temperature below a dew point of the gaseous sterilizing agent, whereby the packaging machine is configured to keep the ready-to-fill packaging containers at the holding section such that the gaseous sterilizing agent will treat areas of the ready-to-fill packaging container having a temperature above the dew point of the gaseous sterilizing agent, and whereby the supply section is a single continuous tunnel structure, separated into an upper disinfection chamber and lower chamber by horizontal baffle plates, where the horizontal baffle plates prevent air from below the horizontal baffle plates to be drawn into the ready-to-fill packaging container where an atmosphere of uniform concentration of the gaseous sterilizing agent is created in the upper disinfection chamber of the single continuous tunnel structure to establish a controlled and even gas distribution into the ready-to-fill packaging container.

2. The packaging machine according to claim 1, wherein the supply section is configured to supply an amount of gaseous sterilizing agent being sufficient to allow continued condensation on the areas of the ready-to-fill packaging container having the temperature below the dew point of the gaseous sterilizing agent, when the ready-to-fill packaging containers enter the holding section from the supply section.

3. The packaging machine according to claim 1, wherein the disinfection/sterilization station further comprises a first venting section downstream the holding section.

4. The packaging machine according to claim 3, wherein the packaging machine is configured to keep the ready-to-fill packaging containers at the first venting section such that the gaseous sterilizing agent inside the ready-to-fill packaging container is removed.

5. The packaging machine according to claim 3, wherein the packaging machine is configured to keep the ready-to-fill packaging containers at the first venting section such that at least a part of a water content of a condensed sterilizing agent is evaporated and removed from the ready-to-fill packaging container.

6. The packaging machine according to claim 3, wherein the disinfection/sterilization station further comprises a film holding section downstream the first venting section.

7. The packaging machine according to claim 6, wherein the packaging machine is configured to keep the ready-to-fill packaging containers at the film holding section such that a condensed film of sterilizing agent, having an increased concentration of sterilizing agent due to an operation of the first venting station, is allowed to treat an inside of the ready-to-fill packaging container.

8. The packaging machine according to claim 6, wherein the disinfection/sterilization station further comprises a drying section downstream the film holding section.

9. The packaging machine according to claim 8, wherein the packaging machine is configured to keep the ready-to-fill packaging at the drying section such that a condensed film of sterilizing agent is evaporated completely from an inside of the ready-to-fill packaging container.

10. A disinfection/sterilizing station for use in a packaging machine, comprising a supply section configured to provide gaseous sterilizing agent into open ends of ready-to-fill packaging containers passing the supply section, and a holding section arranged downstream the supply section, wherein the ready-to-fill packaging containers are controlled to be kept at the supply section such that the sterilizing agent will condense on areas of the ready-to-fill packaging container having a temperature below a dew point of the gaseous sterilizing agent, wherein the ready-to-fill packaging containers are controlled to be kept at the holding section such that the gaseous sterilizing agent will treat areas of the ready-to-fill packaging container having a temperature above the dew point of the sterilizing agent, and wherein the supply section is a single continuous tunnel structure, separated into an upper disinfection chamber and lower chamber by horizontal baffle plates, where the horizontal baffle plates prevent air from below the horizontal baffle plates to be drawn into the ready-to-fill packaging container, where an atmosphere of uniform concentration of the gaseous sterilizing agent is created in the upper disinfection chamber to establish a controlled and even gas distribution into the ready-to-fill packaging container.

11. A method for disinfection/sterilization in a packaging machine configured to form, fill, and seal individual packages, said method comprising:

supplying a gaseous sterilizing agent to an area to be disinfected/sterilized, allowing the gaseous sterilizing agent to at least to some extent condensate at a first sub-area having a temperature below a dew point of the gaseous sterilizing agent, immediately after condensation, keeping a second sub-area, having a temperature above a dew point of the gaseous sterilizing agent, exposed to a remaining gaseous sterilizing agent;

wherein the gaseous sterilizing agent is supplied via a single continuous tunnel structure, separated into an upper disinfection chamber and lower chamber by horizontal baffle plates, where the horizontal baffle plates prevent air from below the horizontal baffle plates to be drawn into a packaging container, where an atmosphere of uniform concentration of the gaseous sterilizing agent is created in the upper disinfection chamber to establish a controlled and even gas distribution into the packaging container.

12. The method according to claim 11, further comprising moving the area to be disinfected/sterilized from a supply section, supplying the gaseous sterilizing agent, to a holding section, at which the second sub-area is exposed to the remaining gaseous sterilizing agent.

13. The method according to claim 11, wherein the gaseous sterilizing agent is hydrogen peroxide.

14. The method according to claim 11, wherein the area to be disinfected/sterilized is a ready-to-fill packaging container being formed, filled, and sealed by the packaging machine.

15. The method according to claim 11, further comprising venting the area to be disinfected/sterilized after keeping the second sub-area exposed to the remaining gaseous sterilizing agent such that at least a part of a water content of a condensed sterilizing agent is evaporated and removed from the area.

16. The method according to claim 15, further comprising keeping the area to be disinfected/sterilized in a controlled atmosphere such that the condensed sterilizing agent, having an increased concentration of sterilizing agent due to a previous venting, is allowed to treat the area.

17. A packaging machine configured to form, fill, and seal individual packages, comprising a disinfection/sterilization station configured to treat ready-to-fill packaging containers passing through said disinfection/sterilization station, wherein the disinfection/sterilization station comprises a supply section configured to provide gaseous sterilizing agent into open ends of the ready-to-fill packaging containers passing the supply section, and a holding section arranged downstream the supply section, wherein the supply section comprises a tunnel structure, and vertically arrange baffle plates and horizontally arranged baffle plates, wherein the vertically arranged baffle plates extend upwards from the horizontally arranged baffle plates, and wherein the horizontally arranged baffle plates are spaced apart in a width direction of the tunnel structure such that the packages ready-to-fill packaging containers can pass between the horizontally arranged baffle plates, whereby the packaging machine is configured to keep the ready-to-fill packaging containers at the supply section such that the gaseous sterilizing agent will condense on areas of the ready-to-fill packaging container having a temperature below a dew point of the gaseous sterilizing agent, whereby the packaging machine is configured to keep the ready-to-fill packaging containers at the holding section such that the gaseous sterilizing agent will treat areas of the ready-to-fill packaging container having a temperature above a dew point of the gaseous sterilizing agent.

18. A packaging machine configured to form, fill, and seal individual packages, comprising a disinfection/sterilization station configured to treat ready-to-fill packaging containers passing through said disinfection/sterilization station, wherein the disinfection/sterilization station comprises a supply section configured to provide gaseous sterilizing agent into open ends of the ready-to-fill packaging containers passing the supply section, and a holding section arranged downstream the supply section, whereby the packaging machine is configured to keep the ready-to-fill packaging containers at the supply section such that the sterilizing agent will condense on areas of the ready-to-fill packaging container having a temperature below a dew point of the gaseous sterilizing agent, whereby the packaging machine is configured to keep the ready-to-fill packaging containers at the holding section such that the gaseous sterilizing agent will treat areas of the ready-to-fill packaging container having a temperature above a dew point of the gaseous sterilizing agent, and whereby a configuration of the disinfection/sterilization station is modular and adjustable, wherein a configuration of a different sections of the disinfection/sterilization station can be adjusted and varied within a geometries of the disinfection/sterilization station.

* * * * *